United States Patent [19]

de Rooij et al.

[11] 4,036,830

[45] July 19, 1977

[54] PROCESS FOR THE RECOVERY OF PURE ε-CAPROLACTAM FROM AN AQUEOUS SOLUTION THEREOF

[75] Inventors: Abraham H. de Rooij, Geleen; Reijer Goettsch, Beek, both of Netherlands

[73] Assignee: Stamicarbon B.V., Geleen, Netherlands

[21] Appl. No.: 681,745

[22] Filed: Apr. 29, 1976

[30] Foreign Application Priority Data

May 1, 1975 Netherlands .......................... 7505130

[51] Int. Cl.$^2$ ........................................... C07D 201/16
[52] U.S. Cl. .............................................. 260/239.3 A
[58] Field of Search ................................. 260/239.3 A

[56] References Cited

U.S. PATENT DOCUMENTS

| 2,221,369 | 11/1940 | Cass ................................ 260/239.3 A |
| 2,692,878 | 10/1954 | Kahr ................................ 260/239.3 A |
| 2,758,991 | 8/1956 | Kretzers et al. ............... 260/239.3 A |
| 2,993,889 | 7/1961 | Muytjens et al. .............. 260/239.3 A |
| 3,850,910 | 11/1974 | Goettsch et al. .............. 260/239.3 A |
| 3,907,781 | 9/1975 | de Rooij et al. .............. 260/239.3 A |
| 3,937,789 | 2/1976 | Donati et al. ................. 260/239.3 A |

*Primary Examiner*—Henry R. Jiles
*Assistant Examiner*—Robert T. Bond
*Attorney, Agent, or Firm*—Cushman, Darby & Cushman

[57] ABSTRACT

A process for recovering substantially pure ε-caprolactam from a contaminated solution thereof is disclosed by concentrating, if needed, the caprolactam content of the solution to about 60–75 weight percent then extracting the concentrated solution with an organic solvent such as benzene or the like, then recovering the resulting caprolactam-laden organic solution.

6 Claims, No Drawings

PROCESS FOR THE RECOVERY OF PURE ε-CAPROLACTAM FROM AN AQUEOUS SOLUTION THEREOF

BACKGROUND OF THE INVENTION

This invention relates to a process for the recovery of substantially pure ε-caprolactam from a contaminated aqueous ε-caprolactam solution.

Such a contaminated solution is obtained, for example, as the wash water obtained when a solution of caprolactam in an organic solvent is washed with water at a pH greater than 4.5, usually 7-9, as described in U.S. Pat. No. 3,850,910.

If a solution of caprolactam in an organic solvent, as obtained in the process according to U.S. Pat. No. 2,758,991, is washed with water at a pH of greater than 4.5, for example at a pH of 7-9, wash water containing contaminated caprolactam is obtained in addition to a solution of caprolactam in the solvent employed.

Although the amount of caprolactam in the wash water obtained from either process is small in relation to the amount of caprolactam dissolved in the organic solvent, we have observed that direct discharge of this caprolactam-laden solution greatly reduces the efficiency of the overall process and hence increases the cost. However, recycling this wash water back to the reaction mixture obtained in the rearrangement of cyclohexanone oxime to caprolactam by means of sulfuric acid, which is proposed in U.S. Pat. No. 3,850,910, according to one experience may adversely affect further processing.

DETAILED DESCRIPTION OF THE INVENTION

We have now found a method to recover the caprolactam in a virtually pure state from this wash water in a simple and economical manner. The process according to the present invention, for recovering virtually pure ε-caprolactam from a contaminated aqueous ε-caprolactam solution, of the type obtained when a solution of ε-caprolactam in an organic solvent is washed with water, is provided when the contaminated solution having a caprolactam content of 60-75% by weight is extracted with benzene or a similar organic solvent, and the caprolactam is recovered from the resulting solution of caprolactam in the extraction agent according to known procedures.

Surprisingly, we have found that the contaminants are retained virtually completely in the aqueous phase in the extraction according to the present invention. In the process according to this invention, an organic solvent such as benzene is used to mean a water-immiscible organic solvent that will provide a distribution coefficient of ε-caprolactam in the water-solvent system which is comparable to that in the waterbenzene system. Examples of such solvents are toluene, xylene, chloroform, methylene chloride, dichloroethane, trichloroethylene 1,1,2-trichloroethane and mixtures thereof.

In many cases, washing the caprolactam solution with water will give a contaminated wash water that contains less than 60% by weight of caprolactam. In order to use the process according to the invention, this wash water may be conveniently concentrated by evaporation to a caprolactam content of 60-75% by weight.

In another embodiment of the process if, as a by-product in the preparation of caprolactam, an ammonium sulfate solution is obtained which is subsequently converted into solid ammonium sulfate, the contaminated wash water containing caprolactam is conveniently concentrated by adding an aqueous ammonium sulfate solution having a high ammonium sulfate content, such as a saturated solution, to the wash water and separating the two layers thus formed. This will produce an ammonium sulfate solution with a lower caprolactam concentration, and a caprolactam-contaminated wash water with a higher caprolactam concentration. Separation into two layers is effected at temperatures of near ambient or slightly higher such as between 15° and 55° C. This method of concentration offers the advantage that no additional evaporating process or equipment is required, since such as apparatus is already required for the evaporation of the ammonium sulfate solution.

As indicated, the contaminated wash water containing the lactam to be recovered can be obtained from several sources, one of which being the process of U.S. Pat. No. 3,850,910 which is a process for the recovery of pure ε-caprolactam containing less than 5 meq. of ionogenic substances per kg. of lactam, the lactam produced by intromolecular conversion of cyclohexanone oxime in the presence of the acid catalyst sulfuric acid, oleum or sulfur trioxide, and extracting the reaction mixture with a water-immiscible organic solvent for the lactam, comprising neutralizing the acid catalyst contained in the solution of the lactam in the organic solvent by adding aqueous ammonia with stirring to the solution of lactam in the organic solvent until the pH of the solution is at least 4.5 which results in:

1. forming an emulsion of an aqueous 15–40% by weight ammonium sulfate solution in the solution of lactam in the organic solvent as the continuous phase;
2. allowing the emulsion to set, forming:
   a. a supernatant aqueous layer and
   b. a heavier organic phase;
3. separating the organic layer (b) from the aqueous layer (a);
4. washing the thus removed organic layer (b) with a counterflow of demineralized water in a weight ratio of 4–20 parts by weight of emulsion per 1 part by weight of demineralized water, thereby removing the residue of the emulsified aqueous salt solution from the organic phase forming an emulsion of water in the organic phase consisting of solvent plus ε-caprolactam; and
5. separating the organic solvent phase containing the ε-caprolactam from the final emulsion of step (4) producing a solution having less than 5 meq. of ammonium sulfate per 1 kg. of dissolved lactam.

Another source is the product resulting from a process for the purification of lactams, which comprises extracting the lactam with water from a solution of the crude lactam in an organic solvent at best only slightly miscible with water, and subjecting the resulting aqueous extract to an aftertreatment with an organic solvent not appreciably miscible with water and in an amount insufficient to dissolve may appreciable amount of lactam as described in U.S. Pat. No. 2,758,991. As both of these patents, commonly assigned to the owners of the present application, are useful in providing detailed descriptions as to the source of the lactam-containing wash water, their disclosures are hereby incorporated by reference.

The extraction of the aqueous solution containing 60–75% by weight of caprolactam in the process according to the invention may be conducted at various temperatures; however suitable temperatures range between 25° and 50° C and are thus preferred.

In the extraction procedure according to the present invention, a solution of virtually pure caprolactam in benzene, or a similar solvent, as listed above, is obtained. The caprolactam can be recovered from this solution by evaporating the solvent, and, if so desired, be further purified to meet very high demands of purity. If the solvent used for the extraction in the process according to the present invention is also used for the recovery of caprolactam from the reaction mixture, as obtained, for instance in the rearrangement of cyclohexanone oxime according to the above-mentioned patents, the solution obtained in the extraction according to the invention is quite suitable for adding, for further processing, to the solution of caprolactam in the organic solvent obtained in the washing treatment. In this way the cost of equipment required to carry out the process is reduced and hardly any caprolactam is lost. The caprolactam solution obtained from the process as described herein contains no more than slight or trace amounts of ionic impurities.

The process of the present invention is further described and illustrated below in the following working example in which all parts and percentages are by weight unless otherwise indicated.

EXAMPLE

A mixture (2300 kilograms) of $\epsilon$-caprolactam and sulfuric acid obtained by Beckmann rearrangement of cyclohexanone oxime (according to known procedures) is neutralized with ammonia water and then separated into two layers. The bottom layer (4382 kilograms) consists of an aqueous ammonium sulfate solution containing 49 kilograms of lactam in solution. The top layer (1424 kilograms) contains 1011 kilograms of lactam.

This top layer is extracted with benzene at 40° C in two series-connected columns. A solution of the lactam in benzene is obtained to which a small amount of a similar solution obtained in the extraction described below, is added via a recycle. A small portion of an aqueous phase is dispersed in the total amount of solution (4821 kilograms); the pH of this aqueous phase is about 4. The pH of the aqueous phase is then raised to about 8 by adding ammonia water (500 ml, 25% by weight). Then the solution of lactam in benzene is washed in a countercurrent with demineralized water (51 kg) in a column packed with ceramic rings (diameter of column 5 cm, effective height of column 5.25 m, diameter of rings about 12 mm), while the solution is pulsated at the rate of 0.5–1 cm per second.

The resulting wash water (148 kilograms, 50% by weight of lactam) is contacted with the ammonium sulfate solution (4382 kilograms) originally obtained as the bottom layer in order to raise the lactam concentration to about 70% by weight, and, subsequently, the mixture is separated into a concentrated layer of wash water (106 kilograms) and a slightly diluted ammonium sulfate layer (4424 kilograms).

The concentrated wash-water layer, which contains about 0.5 kilograms of ammonium sulfate and an amount of organic impurities such that the extinction is about 10 (measured at a concentration of 50% by weight of caprolactam and a layer thickness of 1 cm by means of light of 290 monometers wavelength) is isolated and subjected to extraction with benzene, which yields 336 kg of a solution of lactam in benzene about 22% by weight of the benzene solution being the lactam. The entire amount of this lactam in benzene solution (336 kg, extinction 0.5) was added to the lactam/benzene solution washed with demineralized water, and next the lactam was extracted with water from the total amount of solution to form an aqueous lactam solution (3535 kg) containing 1060 kilograms of lactam and 0.013 kilogram of ionic impurities consisting primarily of ammonium sulfate).

The conductivity of the resulting aqueous lactam solution is about 5 microsiemens and the extinction about 0.45. (The original conductivity of the 4821-kilogram solution before addition of ammonia water and washing is 100 microsiemens and the original extinction of this solution is about 1). If the resulting lactam solution is purified further by means of ion exchange resins, according to known procedures, the capacity of ion exchanger than is otherwise required is considerably lower than would be the case if the washing treatment had not been effected.

The slightly diluted ammonium sulfate layer (4424 kilograms) obtained when the wash water is concentrated still contains a small amount of lactam (49 kilograms), which can be extracted from it by means of benzene. The lactam solution then obtained is recycled and added to the lactam solution obtained in the above-mentioned extraction of the top layer. The remaining aqueous ammonium sulfate solution (1750 kilograms of ammonium sulfate and 2625 kilograms of water) can be processed into solid fertilizer grade ammonium sulfate according to conventional procedures.

What is claimed is:

1. In a process for recovery of pure $\epsilon$-caprolactam from a contaminated aqueous $\epsilon$-caprolactam solution obtained by intramolecular conversion of cyclohexanone oxime with the acid catalyst sulfuric acid, oleum or sulfur trioxide including extracting the reaction mixture after dilution with water and treating with ammonia with a water-immiscible organic solvent for the lactam and washing the lactam in organic solvent for the lactam and washing the lactam in organic solvent with water, the improvement comprising: adjusting the lactam-containing aqueous solution obtained in the said washing step to a caprolactam content of about 60 – 75% by weight, extracting the aqueous lactam-laden solution with an organic solvent immiscible with water and selected from the group consisting of benzene, toluene, xylene, chloroform, methylene chloride, 1,2-dichloroethane, trichloroethylene, 1,1,2-trichloroethane and mixtures thereof, and recovering the extracted caprolactam from the organic solvent.

2. The process according to claim 1 wherein the 60–75% by weight caprolactam-containing aqueous solution is provided by mixing a solution having a lower caprolactam content with a concentrated ammonium sulfate solution and thereafter separating the resulting liquid layer containing ammonium sulfate.

3. The process according to claim 1 wherein the organic solvent used in the extraction step is the same as the organic solvent in which the lactam is dissolved in the water-washing step.

4. The process according to claim 1 wherein the lactam solution obtained in the extraction step is recovered and recycled together with the lactam recovered in the water washing step.

5. In a process for recovery of pure $\epsilon$-caprolactam from a contaminated aqueous $\epsilon$-caprolactam solution obtained by intramolecular conversion of cyclohexanone oxime with the acid catalyst sulfuric acid, oleum or sulfur trioxide including (a) extracting the reaction mixture after dilution with water and treating with ammonia with a water-immiscible organic solvent for the lactam, and (b) washing the lactam in organic solvent with water,
 the improvement of recovering substantially pure ε-caprolactam comprising,
 1. concentrating the lactam-containing aqueous solution from washing step (a) to a caprolactam content of about 60 – 75% by weight,
 2. extracting the aqueous lactam-laden solution with a water-immiscible organic solvent selected from the group consisting of benzene, toluene, xylene, chloroform, methylene chloride, 1,2-dichloroethane, trichloroethylene, 1,1,2-trichloroethane and mixtures thereof forming an aqueous phase containing lactam contaminants therein, and an organic solvent phase containing the caprolactam therein, and
 3. recovering the extracted caprolactam from the organic solvent.

6. The process according to claim 5 wherein the organic solvent is benzene.

* * * * *